United States Patent
Koo et al.

(10) Patent No.: US 6,762,305 B2
(45) Date of Patent: Jul. 13, 2004

(54) HERBICIDALLY ACTIVE PYRIDINE SULFONYL UREA DERIVATIVES

(75) Inventors: Suk-Jin Koo, Yusong-gu (KR); Jin-Ho Cho, Yusong-gu (KR); Jeong-Su Kim, Yusong-gu (KR); Seung-Hun Kang, Seo-gu (KR); Kyung-Goo Kang, Yusong-gu (KR); Dae-Whang Kim, Yusong-gu (KR); Hae-Sung Chang, Yusong-gu (KR); Young-Kwan Ko, Yusong-gu (KR); Jae-Wook Ryu, Yusong-gu (KR)

(73) Assignee: LG Life Sciences, Seoul (KR)

( * ) Notice: Subject to any disclaimer, the term of this patent is extended or adjusted under 35 U.S.C. 154(b) by 0 days.

(21) Appl. No.: 10/731,488

(22) Filed: Dec. 5, 2003

(65) Prior Publication Data

US 2004/0116298 A1 Jun. 17, 2004

Related U.S. Application Data

(62) Division of application No. 10/089,625, filed on Jan. 8, 2003.

(51) Int. Cl.$^7$ ............................................. C07D 213/26
(52) U.S. Cl. ............................................................ 546/293
(58) Field of Search ........................................ 546/293

(56) References Cited

FOREIGN PATENT DOCUMENTS

WO          WO 96/12708          *  5/1996

* cited by examiner

*Primary Examiner*—Debrak Rao
(74) *Attorney, Agent, or Firm*—Peter F. Corless; John B. Alexander; Edwards & Angell, LLP

(57) ABSTRACT

The present invention relates to pyridine sulfonyl urea derivatives, salts or stereochemical isomers thereof showing an effective herbicidal activity in pre- and/or post-emergence treatment in rice farming, or to a method to use thereof, a method for the preparation thereof, an intemediate used for the preparation thereof, and a herbicidal composition comprising same.

2 Claims, No Drawings

HERBICIDALLY ACTIVE PYRIDINE SULFONYL UREA DERIVATIVES

This application is a divisional of application Ser. No. 10/089,625 filed on Jan. 8, 2003 which claims the benefit under 35 U.S.C. 371 of International Application No. PCT/KR00/01138 filed Oct. 12, 2000.

TECHNICAL FIELD

The present invention relates to pyridine sulfonyl urea derivatives represented by the following formula (1):

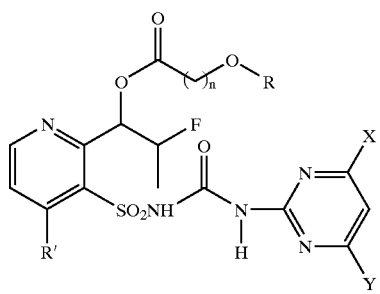

(1)

in which n denotes an integer of from 1 to 3,

R represents H or $C_1$–$C_4$-alkyl,

R' represents H, $C_1$–$C_4$-alkyl, $C_1$–$C_3$-haloalkyl, halogen, or $C_1$–$C_2$-alkoxy, and X and Y independently of one another represent $C_1$–$C_2$-alkyl, $C_1$–$C_2$-alkoxy, $C_1$–$C_2$-haloalkoxy, or halogen, salts or stereochemical isomers thereof showing an effective herbicidal activity in pre- and/or post-emergence treatment in rice farming, or to a method to use thereof, a method for the preparation thereof, an intermediate used for the preparation thereof, and a herbicidal composition comprising same.

BACKGROUND ART

Hitherto, there have been reported a lot of sulfonyl urea derivatives having a herbicidal activity in rice farming. For example, JP 61/191602 discloses a compound represented by the following formula (2):

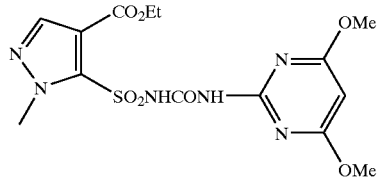

(2)

which has been commercialized as a herbicide for rice farming in the name of Pyrazosulfuron-ethyl.

Korean Patent No. 70675 discloses a compound represented by the following formula (3):

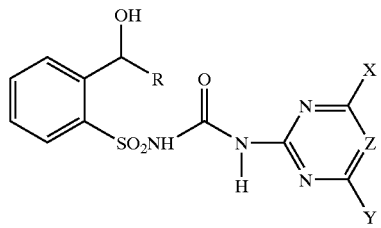

(3)

in which

R represents haloalkyl,

X and Y independently of one another represent $CH_3$, $OCH_3$, Cl, etc., and

Z represents CH or N.

Korean Patent Application No. 91-3014 discloses a herbicidally active sulfonyl urea derivative represented by the following formula (4):

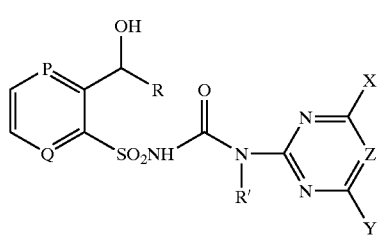

(4)

in which

R, X, Y and Z are defined as the above formula (3),

R' represents H or $CH_3$, and

P and Q independently of one another represent CH or N, but where the aromatic ring including P and Q is benzene or pyridine.

Korean Patent Application No. 93-6915 discloses a herbicidally active pyridine sulfonyl urea derivative represented by the following formula (5):

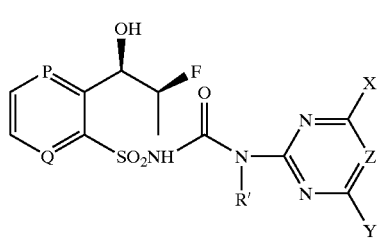

(5)

in which

P, Q, R', X and Y are defined as in the above formula (4),

R represents H, $R^a$—(C=O)— or $R^a$—$X^a$—(C=O)—, wherein $R^a$ represents $C_1$~$C_4$-alkyl, $C_1$~$C_3$-haloalkyl, $C_2$~$C_4$-alkenyl or $C_2$~$C_4$-alkynyl, and $X^a$ represents O, S, NH or $NR^a$.

The existing sulfonyl urea-based herbicidal compounds as explained above show an excellent herbicidal activity against annual and perennial weeds in rice, but have weak activity to barnyardgrass which is the most problematic weed in rice, or cause some phytotoxicity to rice plant. The present inventors claim new pyridine sulfonyl urea derivatives having improved rice safety and superior herbicidal activity against barnyardgrass to the earlier herbicidal compounds, and find great advantages of these new compounds when used as a rice herbicide.

Therefore, one object of the present invention is to provide the pyridine sulfonyl urea derivatives of the above formula (1), salts or stereochemical isomers thereof.

It is another object of the present invention to provide a process for the preparation of the compound of formula (1).

It is further object of the present invention to provide a novel intermediate which is used for the preparation of the compound of formula (1).

It is further object of the present invention to provide a method to use the compound of formula (1) as a herbicide for paddy rice, and a herbicidal composition comprising same.

The present invention will be explained in more detail hereinafter.

DISCLOSURE OF INVENTION

The present invention relates to a compound of the following formula (1):

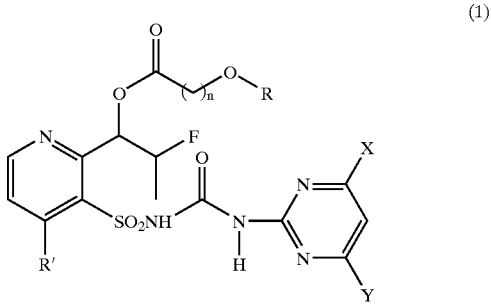

(1)

in which
n denotes an integer of from 1 to 3,
R represents H or $C_1$–$C_4$-alkyl,
R' represents H, $C_1$–$C_4$-alkyl, $C_1$–$C_3$-haloalkyl, halogen, or $C_1$–$C_2$-alkoxy, and
X and Y independently of one another represent $C_1$–$C_2$-alkyl, $C_1$–$C_2$-alkoxy, $C_1$–$C_2$-haloalkoxy, or halogen.

Among the compound of formula (1) which shows an excellent selectivity to rice plant and herbicidal activity to barnyardgrass and thus, can be advantageously used as a herbicide for rice farming, the preferred compounds include those wherein n denotes an integer of 1 or 2, R represents H or methyl, R' represents H, halogen or methyl, and X and Y each represents methoxy.

Particularly preferred compounds include those wherein n denotes an integer of 1 or 2, R represents methyl, R' represents H, Cl, Br or methyl, and X and Y each represents methoxy.

Typical examples of the compound of formula (1) according to the present invention are exemplified as follows:

N-[(4,6-dimethoxypyrimidin-2-yl)aminocarbonyl]-2-(2-fluoro-1-methoxy acetoxy-n-propyl)pyridine-3-sulfonamide.

N-[(4,6-dimethoxypyrimidin-2-yl)aminocarbonyl]-2-(2-fluoro-1-hydroxy acetoxy-n-propyl)pyridine-3-sulfonamide.

N-[(4,6-dimethoxypyrimidin-2-yl)aminocarbonyl]-2-(2-fluoro-1-(3-hydroxy propion)oxy-n-propyl)pyridine-3-sulfonamide.

N-[(4,6-dimethoxypyrimidin-2-yl)aminocarbonyl]-2-(2-fluoro-1-(3-methoxypropion)oxy-n-propyl)pyridine-3-sulfonamide.

N-[(4,6-dimethoxypyrimidin-2-yl)aminocarbonyl]-4-methyl-2-(2-fluoro-1-methoxyacetoxy-n-propyl)pyridine-3-sulfonamide.

N-[(4,6-dimethoxypyrimidin-2-yl)aminocarbonyl]-4-chloro-2-(2-fluoro-1-methoxyacetoxy-n-propyl)pyridine-3-sulfonamide.

N-[(4,6-dimethoxypyrimidin-2-yl)aminocarbonyl]-4-bromo-2-(2-fluoro-1-methoxyacetoxy-n-propyl)pyridine-3-sulfonamide.

Since the compound of formula (1) has two asymmetric carbons therein, they can exist as an erythro or threo isomer, or mixtures thereof. The compound of the present invention shows a stronger activity in the erythro form, but the mixtures thereof in a suitable mixing ratio also exhibit a sufficient activity.

The compound of formula (1) according to the present invention can be prepared by a process characterized in that a compound represented by the following formula (6):

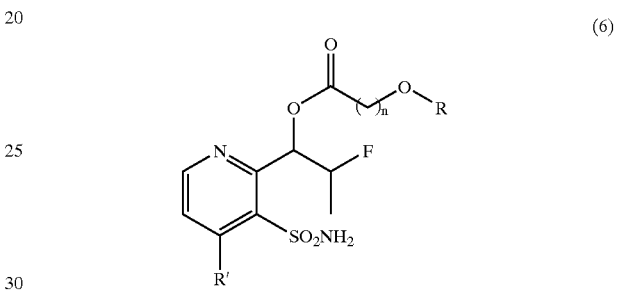

(6)

in which
n, R and R' are defined as in the above formula (1), is reacted in a solvent optionally in the presence of a base with a compound represented by the following formula (7):

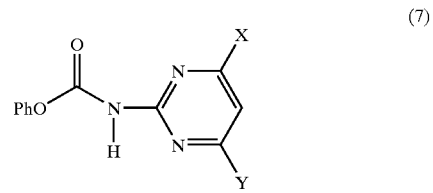

(7)

in which
X and Y are defined as in the above formula (1). Therefore, it is another object of the present invention to provide such a preparation process.

The compound of formula (6) used as a starting material in the process according to the present invention can exist as an erythro isomer, threo isomer, or mixtures thereof. The stereo-chemical configuration of the desired compound of formula (1) may be determined in line with the configuration of compound (6).

Any solvent which does not adversely affect the reaction can be used in the above process, but preferably tetrahydrofuran, acetone, acetonitrile, dioxane, methylene chloride, toluene, butanol, pyridine, dimethylformamide, etc. can be used. The above process is carried out preferably in the presence of a small amount of strong base, such as for example, triethylamine, hexamethylenetetramine, pyridine, DBU or DABCO (wherein DBU means 1,8-diazabicyclo[5,4,0]undec-7-ene and DABCO means 1,4-diazabicyclo[2,2,2]octane, and they have the same meaning throughout the present specification), etc., and the reaction temperature may be preferably maintained in the range of 10~80° C. The specific reaction conditions can be referred to U.S. Pat. No. 4,443,245 which discusses similar reactions, and after the reaction is completed, the desired compound can be obtained through the acid-treatment procedure as described in EP 044,807. If a highly pure compound is required, it is desirable to use HPLC technique.

The compound of formula (7) was known and can be easily prepared according to the process described in Korean Patent No. 70,675.

The compound of formula (6) is a novel intermediate which is provided first by the present invention. Therefore, it is another subject matter to be provided by the present invention. The compound of formula (6) can be prepared by treating a compound represented by the following formula (8):

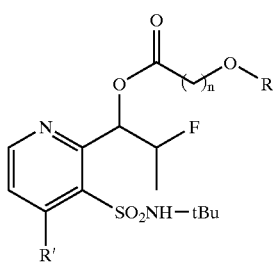
(8)

in which, n, R and R' are defined as formula (1), with trifluoroacetic acid (TFA) to eliminate the t-butyl group therefrom.

If the compound of formula (8) is stirred in the solvent of trifluoroacetic acid(TFA) at 0~80° C., the t-butyl group is eliminated to give the sulfonamide compound of formula (6). When the compound of formula (6) thus obtained is present in the form of an erythro-threo mixture, it may be resolved by column chromatography, HPLC or preparative-TLC method to give pure erythro or threo compound.

The compound of formula (8) may also be prepared by acylating a compound represented by the following formula (9) according to a conventional manner:

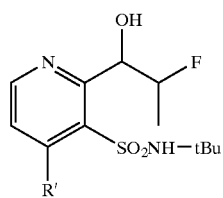
(9)

in which R' is defined as in the above formula (1).

The compound of formula (9) may be prepared by selectively reducing a compound represented by the following formula (10):

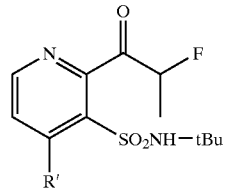
(10)

in which R' is defined as in the above formula (1), using a suitable reducing agent, such as for example, DIBAL H(Diisobutylaluminum hydride), NaBH$_4$, LiAlH$_4$, BH$_3$.

The compound of formula (1) as can be prepared as explained above is more definitely exemplified individually in the following Table 1.

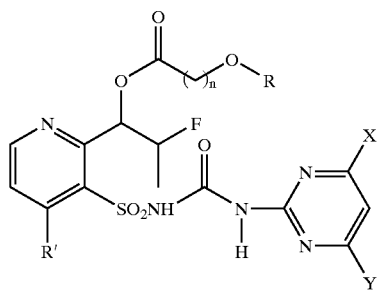

TABLE 1

| R' | n | R | X | Y | m.p.(° C.) |
|---|---|---|---|---|---|
| Cl | 1 | CH$_3$ | Ome | OMe | 135–140 |
| Br | 1 | CH$_3$ | Ome | OMe | 87–89 |
| Br | 1 | H | Ome | OMe | |
| OCH$_3$ | 1 | CH$_3$ | Ome | OMe | |
| CH$_3$ | 1 | CH$_3$ | Ome | OMe | 156–158 |
| CF$_3$ | 1 | CH$_3$ | Ome | OMe | |
| H | 1 | H | Ome | OMe | 157–158 |
| CH$_3$ | 2 | CH$_3$ | Ome | OMe | |
| H | 1 | CH$_3$ | Ome | OMe | 175–177(erythro) |
| H | 1 | CH$_3$ | Ome | OMe | 152–154(threo) |
| H | 1 | CH$_3$ | Ome | Cl | |
| H | 1 | CH$_3$ | Me | Me | |
| H | 2 | H | Ome | OMe | 147–148 |
| H | 2 | CH$_3$ | Ome | OMe | 145–146 |

The compound of formula (1) according to the present invention may exist as a suitable salt and is utilizable as a herbicide in that form. The salt can be prepared by a conventional method known per se, for example, by contacting the compound of formula (1) with a solution containing hydroxide, alkoxide, or carbonate of alkali metal or alkaline earth metal. Otherwise, the salt may be prepared by using an amine compound in the similar manner.

Various salts can also be obtained by exchanging the cation of the salt of compound of formula (1) by another one. Cation exchange is carried out by directly contacting a salt of the compound of formula (1), for example, alkali metal salt or quarternary amine salt in aqueous solution with a solution containing the cation to be newly combined. This method is the most effective when the resulting salt containing the newly combined cation is insoluble in water. Ion exchange can also be carried out by subjecting a salt of the compound of formula (1), for example, alkali metal salt or quarternary amine salt in aqueous solution to a column filled with cation exchange resin containing the cation to be newly combined. In this case, the cation in the resin is exchanged with the cation of the original salt and the desired salt newly formed is eluted from the column. This method is particularly effective when the resulting salt is water-soluble, that is, sodium, potassium or calcium salt.

Further, the compound of formula (1) is conveniently used as a herbicidal agent when it is present in the form of mixtures or complexes with urea or amide compound. Those mixtures or complexes may be prepared according to the typical methods.

The preparation or conversion process as briefly summarized above may be easily carried out by a person skilled in the area of organic synthesis or synthesis of sulfonyl urea derivatives. All the processes designed from the present description by conventional modifications fall within the scope of the present invention.

As stated already, the pyridine sulfonyl urea derivative of formula (1) according to the present invention can be used as a herbicidal agent. Therefore, the utilities and formulations are explained below.

[Utility]

Since the compound of formula (1) has an excellent selectivity for rice plant as well as a potent herbicidal activity, it can be used as a herbicide for paddy rice and can be contained as an active ingredient in herbicidal composition.

Test results indicate that the compound of formula (1) is highly active as a herbicide for pre- or post-emergence treatment in paddy and upland.

The rates of application of the active compound of the invention are determined by a number of factors, including the types of weeds to be controlled, weather, climate, formulations selected, mode of application, size of weeds, etc. In general terms, the subject compounds should be applied at levels of around 1 g to 1 kg/ha, the lower rates being suggested for use on soils having a low organic matter content or sandy soil, for young plants, or for situations where only short-term persistence is required. Particularly, the subject compounds may be used effectively in rice to control various weeds including barnyardgrass, annual broadleaf and sedge weeds as well as perennial weeds.

The compounds of the present invention may be used alone or as two-, three-, or four-way combinations together with the existing herbicides.

[Formulation]

In the present invention, the compound of formula (1) is used in the form of a conventional composition. If necessary, the compound of formula (1) is applied to plant, soil, or water surface in combination with carriers, surfactants, adjuvants, or other additives which are conveniently used in the technical field of formulation.

Suitable carriers and additives may be a solid or a liquid and include those components effectively used in the field of formulation, such as for example, natural or synthetic inorganic substances, solvents, dispersants, wetting agents, adhesive agents, thickening agents, binding agents, etc.

The composition comprising the compound of formula (1) is preferably applied to soil in the form of a solid, for example, a granule, or liquid (soil treatment). Otherwise, the composition comprising the compound of formula (1) may be applied directly to a plant foliage (foliar treatment). Frequency and rate of application are varied depending on the biological characteristics of plants, weather, soil types, and other environmental conditions.

The active ingredient-containing combinations in unmodified form can be used together with the known adjuvants conveniently used in the field of formulation. They are formulated according to the known methods to emulsifiable concentrates, liquid formulations which can be diluted, liquid hydrates which can be directly applied to water surface, developing agent for water surface, emulsions, hydrates, powders, dusts, granules or tablets. Application methods such as spraying, dusting, broadcasting, etc. and characteristics of the composition are selected to be compatible with the purpose of use and environments. The rate of application of the active ingredient-containing combination varies generally in the range of from 1 g to 1 kg a.i./ha, preferably from 10 g to 30 g a.i./ha.

For example, the active ingredient may be intimately mixed and/or pulverized with extenders[e.g. solvents, solid carriers and if desired, surface-active compounds (surfactants)] according to the known methods to give the combinations.

Possible solvents include the following: aromatic hydrocarbons such as xylene mixtures or substituted naphthalenes; alcohols and glycols, and their ethers and esters such as ethanol, ethylene glycol, ethylene glycol monomethyl or monoethyl ether; ketones such as cyclohexanone; strongly polar solvents such as N-methyl-2-pyrrolidone, dimethylsulfoxide or dimethylformamide; optionally epoxidised vegetable oils such as epoxidised coconut oil or soybean oil; and water. These solvents can be used as emulsifying agents, solvents for liquid formulation or cosolvents for granule formulation.

The solid carriers used e.g. for dusts and granules, are normally pulverized natural mineral fillers such as talc, kaolin, montmorillonite, pyrophyllite, bentonite, calcite, or adsorptive carriers such as zeolite, or sand. In addition, a great number of prepulverized materials of inorganic or organic nature can be used.

Depending on the nature of the compound of formula (1) to be formulated, suitable surface-active compounds are nonionic, cationic and/or anionic surfactants having good dispersing, wetting and lubricating properties. The term "surfactants" will also be understood as comprising mixtures of surfactants.

The herbicidal compositions, broadly, contain 0.1 to 99% by weight, preferably 0.1 to 95% by weight of the compound of formula (1), 99.9 to 1% by weight, preferably 99.9 to 5% by weight of solid or liquid additives, and 0 to 25% by weight, preferably 0.1 to 25% by weight of surfactant.

These compositions fall within the scope of the present invention.

BEST MODE FOR CARRYING OUT THE INVENTION

The process for the preparation and use of the compound according to the present invention will be more specifically explained in the following Examples. However, it should be understood that these Examples are intended to illustrate the present invention but not in any manner to limit the scope of the present invention. Unless otherwise stated, C18 silica (25–40 µm, 50 ml) column equilibrated with acetonitrile/water=10/90(v/v) was used as the stationary phase of column chromatography in the following Examples.

EXAMPLE 1

Synthesis of erythro-N-t-butyl-4-methyl-2-(2-fluoro-1-hydroxy-n-propyl)pyridine-3-sulfonamide Erythro-N-t-butyl-2-(2-fluoro-1-hydroxy-n-propyl) pyridine-3-sulfonamide (2.55 g) was dissolved in THF(150 ml) which had been well purified and then 2.5N n-BuLi(13.4 ml) was slowly added thereto under nitrogen gas at −78° C.

The reaction temperature was raised to −20° C. and cooled down to −78° C. again. CuI(2.10 g) was introduced into another flask and the lithium salt prepared above was reversely added to this flask. After 10 minutes, CH₃I(0.83 ml) was added, the resulting mixture was stirred for 30 minutes at −78° C., and the reaction was quenched with NH₄Cl solution. Ethyl acetate was added to the reaction solution to separate the organic layer. The aqueous layer was extracted with ethyl acetate, and then the organic layers were combined, dried(MgSO₄), filtered and concentrated to give a crude product. This crude product was subjected to column chromatography (Moving phase: ethyl acetate/n-hexane=1/2, v/v) to give 0.5 g of the pure title compound.

$^1$H NMR(200 MHz, CDCl₃): δ 8.55 (d, 1H, J=5 Hz), 7.24 (d, 1H, J=5 Hz), 6.1 (br s, 1H), 4.6–4.9 (m, 3H), 2.76 (s, 3H), 1.35 (dd, 3H, $J_1$=25 Hz, $J_2$=6 Hz), 1.26 (s, 9H).

EXAMPLE 2

Synthesis of erythro-4-methyl-2-(2-fluoro-1-methoxy-acetoxy-n-propyl)pyridine-3-sulfonamide Erythro-N-t-butyl-4-methyl-2-(2-fluoro-1-hydroxy-n-propyl)pyridine-3-sulfonamide(0.7 g) was dissolved in THF (10 ml) and methoxyacetylchloride(0.32 g) was added thereto. 60% NaH(0.13 g) was added at 0° C. and the resulting mixture was stirred for 2 hours at room temperature. The reaction was quenched with saturated aqueous NH₄Cl solution and extracted with ethyl acetate. The organic layer was dried(MgSO₄), filtered and concentrated, and the residue was subjected to column chromatography (Moving phase: ethyl acetate/n-hexane=1/3, v/v) to give erythro-N-t-butyl-4-methyl-2-(2-fluoro-1-methoxyacetoxy-n-propyl)pyridine-3-sulfonamide(0.7 g).

To the resulting product was added CF₃CO₂H(10 ml) and the mixture was stirred for 1 hour at 60~65° C. The reaction solution was concentrated under reduced pressure and the residue was dissolved in methylene chloride and washed with aqueous sodium bicarbonate solution. The organic layer was dried(MgSO₄), filtered and concentrated, and the residue was subjected to column chromatography (Moving phase: ethyl acetate/methylene chloride=1/7~1/1, v/v) to give 0.37 g of the pure title compound.

$^1$H NMR(200 MHz, CDCl₃): δ 8.57 (d, 1H, J=5 Hz), 7.24 (d, 1H, J=5 Hz), 6.85~6.95 (m, 1H), 5.65 (br s, 2H), 4.9~5.3(m, 1H), 4.13 (s, 2H), 3.41 (s, 2H), 2.72 (s, 3H), 1.55 (dd, 3H, $J_1$=25 Hz, $J_2$=6 Hz).

EXAMPLE 3

Synthesis of erythro-N-t-butyl-4-chloro-2-(2-fluoro-1-hydroxy-n-propyl)pyridine-3-sulfonamide Erythro-N-t-butyl-2-(2-fluoro-1-hydroxy-n-propyl)pyridine-3-sulfonamide(0.29 g) was dissolved in THF(10 ml) which had been well purified and then 2.5N n-BuLi(1.52 ml) was slowly added thereto under nitrogen gas at −78° C. The reaction temperature was raised to −20° C. and cooled down to −78° C. again. NCS(N-chlorosuccinimide)(0.2 g) dissolved in THF(5 ml) was slowly added to the reaction solution. After 30 minutes, the reaction was quenched with saturated aqueous ammonium chloride solution. Ethyl acetate was added to the reaction solution to separate the organic layer. The aqueous layer was extracted once more with ethyl acetate, and then the organic layers were combined, dried (MgSO₄), filtered and concentrated to give a crude product. This crude product was subjected to column chromatography (Moving phase: ethyl acetate/n-hexane=1/2, v/v) to give 0.18 g of the pure title compound.

$^1$H NMR(200 MHz, CDCl₃): δ 8.61 (d, 1H, J=5 Hz), 7.50 (d, 1H, J=5 Hz), 6.05~6.15 (br s, 1H), 5.2 (br s, 1H), 4.6~4.9 (m, 2H), 1.35 (dd, 3H, $J_1$=25 Hz, $J_2$=6 Hz), 1.25 (s, 9H).

EXAMPLE 4

Synthesis of erythro-N-t-butyl-4-chloro-2-(2-fluoro-1-methoxyacetoxy-n-propyl)pyridine-3-sulfonamide Erythro-N-t-butyl-4-chloro-2-(2-fluoro-1-hydroxy-n-propyl)pyridine-3-sulfonamide(0.75 g) was dissolved in THF(10 ml) and methoxyacetylchloride(0.33 g) was added thereto. The reaction solution was cooled down to 0° C. and 60% NaH (0.13 g) was added. The resulting solution was warmed to room temperature and stirred for 2 hours.

What is claimed is:

1. A compound of the following formula (6):

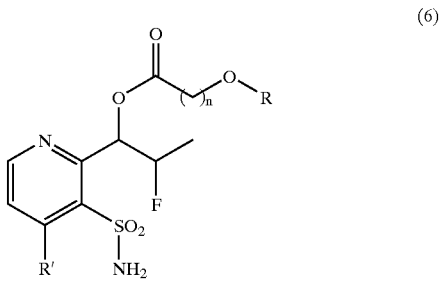

in which n denotes an integer of from 1 to 3,

R represents H or $C_1$–$C_4$-alkyl, and

R' represents H, $C_1$–$C_4$-alkyl, $C_1$–$C_3$-haloalkyl, halogen, or $C_1$–$C_2$-alkoxy.

2. The compound of claim 1 which is 2-(fluoro-1-methoxyacetoxy-n-propyl)pyridine-3-sulfonamide.

* * * * *